US008466278B2

(12) United States Patent
Elewaut et al.

(10) Patent No.: US 8,466,278 B2
(45) Date of Patent: Jun. 18, 2013

(54) CARBOXYETHYLATED CYCLODEXTRIN POLYSULFATES USEFUL AS MEDICAMENTS

(75) Inventors: Dirk Elewaut, Heusden (BE); August Lodewijk Verbruggen, Nazareth-Eke (BE)

(73) Assignee: Arcarios B.V., Rotterndam (NL)

( * ) Notice: Subject to any disclaimer, the term of this patent is extended or adjusted under 35 U.S.C. 154(b) by 245 days.

(21) Appl. No.: 13/120,176

(22) PCT Filed: Sep. 22, 2009

(86) PCT No.: PCT/EP2009/062277
§ 371 (c)(1),
(2), (4) Date: Mar. 22, 2011

(87) PCT Pub. No.: WO2010/031876
PCT Pub. Date: Mar. 25, 2010

(65) Prior Publication Data
US 2011/0172182 A1    Jul. 14, 2011

(30) Foreign Application Priority Data
Sep. 22, 2008    (EP) .................................... 08164818

(51) Int. Cl.
C08B 37/16    (2006.01)
C08B 37/00    (2006.01)
C07H 1/00    (2006.01)
C07H 3/00    (2006.01)
A01N 43/04    (2006.01)
A61K 31/715    (2006.01)

(52) U.S. Cl.
USPC .............................. 536/103; 536/124; 514/58

(58) Field of Classification Search
None
See application file for complete search history.

(56) References Cited

U.S. PATENT DOCUMENTS
6,930,098 B2    8/2005    Veys et al.

FOREIGN PATENT DOCUMENTS
| | | |
|---|---|---|
| EP | 0 531 016 A2 | 3/1993 |
| WO | 89/06536 A1 | 7/1989 |
| WO | 93/09790 A1 | 5/1993 |
| WO | 96/31220 A1 | 10/1996 |
| WO | 01/12202 A2 | 2/2001 |
| WO | 01/25402 A1 | 4/2001 |
| WO | 2005/014026 A2 | 2/2005 |

OTHER PUBLICATIONS

Vippagunta et al. Advanced Drug Delivery Reviews 48 (2001) 3-26.*
Butoescu et al. European Journal of Pharmaceutics and Biopharmaceutics 73 (2009) 205-218.*
Cornelissen, M. et al.; The Study of Representative Populations of Native Aggrecan Aggregates Synthesized by Human Chondrocytes In Vitro; J. Tiss. Cult. Meth.; 1993; pp. 139-146; 15; Tissue Culture Association.
Groeneboer, S. et al.; Cyclodextrin polysulphate protects articular cartilage in experimental lapine knee osteoarthritis; Osteoarthritis and Cartilage; 2008; pp. 986-993; 16; Osteoarthritis Research Society International.
Guo, J. et al; Culture and Growth Characteristics of Chondrocytes Encapsulated in Alginate Beads; Connective Tissue Research; 1989; pp. 277-297; vol. 19; Gordon and Breach, Science Publishers, Inc.
Jin, L.J. et al.; Comparistion of chiral recognition capabilities of cyclodextrins for the separation of basic drugs in capillary zone electrophoresis; Journal of Chromatography B; 1998; pp. 257-266; 708; Elsevier Science B.V.
Jy, W. et al.; A Flow Cytometric Assay of Platelet Activation Marker P-Selectin (CD62P) Distinguishes Heparin-induced Thrombocytopenia (HIT) from HIT with Thrombosis (HITT); Thromb Haemost; 1999; pp. 1255-1259; 82; Schattauer Verlag, Stuttgart.
Wang, L. et al.; Flow cytometric analysis of the human articular chondrocyte phenotype in vitro; Journal of the OsteoArthritis and Cartilage; 2001; pp. 73-84; 9; OsteoArthritis Research Society International.
International Search Report and Written Opinion dated Jul. 12, 2009 pertaining to International application No. PCT/ EP2009/062277.

* cited by examiner

Primary Examiner — Layla Bland
(74) Attorney, Agent, or Firm — Dinsmore & Shohl LLP

(57) ABSTRACT

This invention relates to novel β-cyclodextrin polysulfate compounds comprising from one to three 2-carboxyethyl substituents, and at least two sulfates groups per glucopyranose unit, which are useful as active ingredients for the treatment and/or prophylaxis of degenerative joint diseases, osteoarthritis, articular rheumatism, arthrosis or degenerative arthritis, or for the treatment of heparin-induced thrombocytopenia, or for cartilage repair or connective tissue repair.

14 Claims, 3 Drawing Sheets

CARBOXYETHYLATED CYCLODEXTRIN POLYSULFATES USEFUL AS MEDICAMENTS

FIELD OF THE INVENTION

The present invention relates to carboxyalkylated β-cyclodextrin polysulfates and salts thereof, a process for their preparation, a pharmaceutical composition comprising a therapeutically effective amount of these compounds and the use of such carboxyalkylated β-cyclodextrin compounds as active ingredients, alone or in combination with other therapeutic agents, in a method for the treatment and/or prophylaxis of degenerative joint diseases, in particular osteoarthritis, or for the treatment of heparin-induced thrombocytopenia, or for cartilage repair or connective tissue repair.

BACKGROUND OF THE INVENTION

Cyclodextrins make up a family of cyclic oligo- and polysaccharides containing 5 or more D-glucopyranoside units linked through a 1-4 glycosidic bonds. The most typical cyclodextrins contain 6 to 8 glucopyranoside units in a ring, creating a cone shape. Within this family, β-cyclodextrin have 7 glucopyranoside units in a ring. Classic sulfation procedures result in the sulfation of one, two or three hydroxyl groups of the glucopyranoside units.

Some medicinal uses of polysulphated cyclodextrins are already known in the art. For instance U.S. Pat. No. 6,930,098 teaches treating a human afflicted with arthrosis by administering a composition consisting essentially of a polysulphated cyclodextrin or an addition salt thereof, in combination with one or more non-toxic pharmaceutically acceptable excipients; preferably the dosage for such treatment ranges from 50 mg to 1,500 mg per day. According to Osteoarthritis and Cartilage (2008) 16:986-993, β-cyclodextrin polysulfate (CDPS), subcutaneously administered in a rabbit model of experimental osteoarthritis (OA) reduced the cartilage lesions and osteocyte formation in the affected joints. These data suggest that CDPS positively affects the tissue pathology underlying OA and this agent can therefore be classified as a structure or disease modifying OA drug.

Apart from the chondroprotective capacities, other characteristics of CDPS are described in the literature. Polysulfated cyclodextrins have been shown to possess important biological activities similar to those of heparin which can be explained by the similarities in their molecular structure. Apart from a strong binding affinity for a fibroblast growth factor, an anti-angiogeneic activity and a capacity of inhibiting cellular invasion by HIV retro virus, both polysaccharides possess anticoagulant properties and CDPS may elicit heparin-induced thrombocytopenia.

In vitro studies concerning CDPS and coagulation show prolongation of thrombin clotting times and a reduction in thrombus formation. Such biological activities were clearly shown to be related to the molecular structure of the polysaccharide and varied following distinct modifications. The introduction of distinct alkyl groups for example, did not prolong the activated partial thromboplastin time (aPTT) in vitro suggesting a reduced anti-coagulant activity compared to CDPS.

Next, the potency to induce heparin-induced thrombocytopenia (hereinafter referred as HIT) and thromboembolic accidents through cross reaction with heparin/platelet factor IV antibodies is a matter of concern. These antibodies can arise occasionally when activated thrombocytes release platelet factor IV (PF4) during heparin treatment. Heparin then forms a complex with PF4 that acts as an antigen which triggers the production of auto-antibodies. These anti-bodies bind to the complex via their F(ab)' region and to the FcγRII (IgG CD32) of other platelets via the Fc portion thereby initiating platelet activation, aggregation and generation of platelet-derived microparticles. These pro-coagulant particles are likely to induce the thrombotic complications of HIT. It has been shown that some low molecular weight heparins as well as other sulphated polysaccharides, e. g. chondroitin polysulphates, can also bind to HIT antibodies in the presence of PF4 and that the reactivity is dependant on their molecular weight and the sulfation grade. Only a subset of patients will produce antibodies with platelet-activating properties after heparin therapy. Some of the later will develop thrombocytopenia and even less will develop thrombosis.

Thus, it is one problem to be addressed by the presently claimed invention to provide novel therapeutic agents with a preserved chondro-protective capacity, a reduced effect on coagulation and a reduced risk for heparin-induced thrombocytopenia.

It is another problem to be addressed by the presently claimed invention to provide novel therapeutic agents that are suitable for the prevention of platelet aggregation and vascular thrombosis in individuals afflicted with HIT syndrome.

It is another problem to be addressed by the present invention to provide novel therapeutic agents which can be used to treat HIT syndrome without inducing anti-coagulant activity.

Furthermore, it is another problem to be addressed by the presently claimed invention to provide novel therapeutic agents which can be used to treat HIT syndrome without inducing platelet activation or thrombosis in the presence of heparin- and platelet factor IV-complex reactive antibodies.

It is another problem to be addressed by the presently claimed invention to provide novel therapeutic agents which can be used for the treatment and/or prophylaxis of degenerative joint diseases such as osteoarthritis, articular rheumatism, arthrosis or degenerative arthritis, or for cartilage repair or connective tissue repair.

SUMMARY OF THE INVENTION

It has been unexpectedly found that 2-carboxyethyl-β-cyclodextrin polysulfate derivatives (CE-CDPS), and salts thereof, and analogues thereof (especially the carboxymethyl, carboxypropyl and carboxybutyl analogues), do not significantly activate platelets and, thus, show minimal potential to induce heparin-related thrombo-embolic accidents in vivo. When CE-CDPS was tested on collagenase-induced knee-osteoarthritis in mice, the compound prevented cartilage proteoglycan depletion in the osteoarthritis knee joints of mice while at the same time not showing negative side effects such as heparin-induced thrombocytopenia.

DETAILED DESCRIPTION OF THE INVENTION

Thus, in a first aspect the present invention relates to novel β-cyclodextrin compounds represented by the structural formula (I)

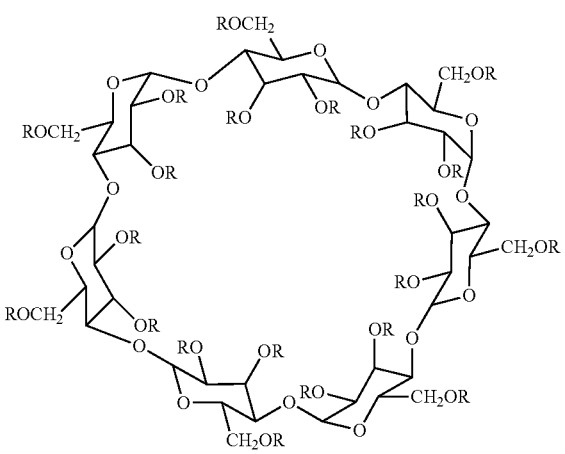

wherein each R is independently chosen to be either —CH$_2$—CH$_2$—COOH or —CH$_2$—COOH or —CH$_2$—CH(CH$_3$)—COOH or —CH$_2$—CH(C$_2$H$_5$)—COOH or —SO$_3$H or H, with the proviso that from one to three R represent —CH$_2$—CH$_2$—COOH, or from 1 to 4 R represent —CH$_2$—COOH or —CH$_2$—CH(CH$_3$)—COOH or —CH$_2$—CH(C$_2$H$_5$)—COOH, and with the proviso that at least two R per glucopyranose unit represent —SO$_3$H, and the corresponding pharmaceutically acceptable salts thereof and/or solvates thereof. Particularly preferred salts of these acidic compounds include the potassium, sodium and calcium salts.

The aforementioned groups can be located in any of the aforementioned positions R on the β-cyclodextrin molecule. According to a particular embodiment of the present invention, the carboxyethyl moiety —CH$_2$—CH$_2$—COOH may be present either at carbon 2 or at carbon 6 of a D-glucopyranose unit of the β-cyclodextrin molecule. According to another particular embodiment of the present invention, three of the seven D-glucopyranose units of the β-cyclodextrin molecule are each substituted with a carboxyethyl moiety —CH$_2$—CH$_2$—COOH. According to another particular embodiment of the present invention, 3 or 4 of the seven D-glucopyranose units of the β-cyclodextrin molecule are each substituted with a carboxymethyl moiety —CH$_2$—COOH or with a carboxypropyl moiety —CH$_2$—CH(CH$_3$)—COOH or with a carboxybutyl moiety —CH$_2$—CH(C$_2$H$_5$)—COOH.

According to a particular embodiment of the present invention, each R is independently chosen to be either —CH$_2$—CH$_2$—COOH or —SO$_3$H or H, with the proviso that two to three R represent —CH$_2$—CH$_2$—COOH, and at least seven, preferably at least ten, more preferably at least fourteen, most preferably at least sixteen, R represent —SO$_3$H. According to another particular embodiment of the present invention, each R is independently chosen to be either —CH$_2$—CH$_2$—COOH or —SO$_3$H or H, with the proviso that all R together (i.e. the whole set of 21 groups) represent three groups —CH$_2$—CH$_2$—COOH and either sixteen groups —SO$_3$H and two hydrogen atoms, or seventeen groups —SO$_3$H and one hydrogen, or eighteen groups —SO$_3$H (in the latter case, four of the seven D-glucopyranose units of the β-cyclodextrin compound are substituted with three —SO$_3$H groups, and three of the seven D-glucopyranose units of the (β-cyclodextrin compound are substituted with two —SO$_3$H groups).

The invention encompasses the β-cyclodextrin compounds represented by the structural formula (I) in their acidic form or in the form of any of the pharmaceutically acceptable salts thereof. In the acidic form, the —COO$^-$ and —SO$_3^-$ functions are in —COOH— and —SO$_3$H form, respectively.

The expression "pharmaceutically acceptable salt" refers to compounds represented by the structural formula (I) in which one or more of the –COO$^-$ and —SO$_3^-$ functions (anions) are ionically associated to a pharmaceutically acceptable counter-ion such as, but not limited to, a metal cation. The preferred salts according to the present invention are those in which the cation is chosen from alkali metal cations and even more preferably those in which the cation is Na$^+$ or K$^+$ Alternatively a suitable pharmaceutically acceptable salt may be a calcium salt.

The term "solvate" according to the present invention is to be understood as meaning any form of compounds represented by the structural formula (I), or pharmaceutically acceptable salts thereof, in which they are non-covalently bound to a solvent molecule (preferably a polar solvent). This especially includes hydrates and alcoholates, e. g. methanolates or ethanolates. Solvates, preferably hydrates, of the compounds represented by the structural formula (I) can be obtained by standard solvating procedures well known to those skilled in the art.

In another aspect the present invention relates to a process for the preparation of carboxyalkylated β-cyclodextrin compounds represented by the structural formula (I).

In a particular embodiment, the process is characterised in that a β-cyclodextrin compound represented by the structural formula

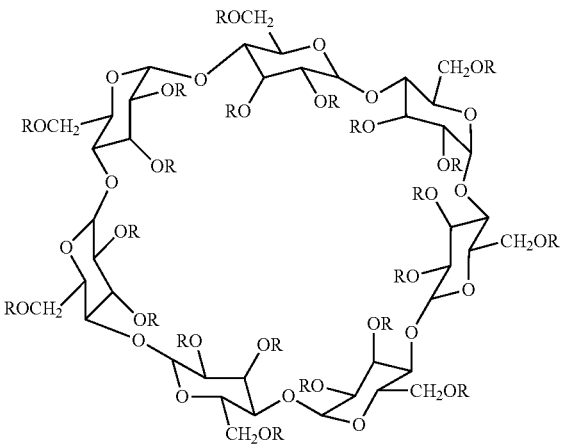

wherein each R is independently chosen to be either —CH$_2$—CH$_2$—COOH or —CH$_2$—COOH or —CH$_2$—CH(CH$_3$)—COOH or —CH$_2$—CH(C$_2$H$_5$)—COOH or H, with the proviso that from one to three R represent —CH$_2$—CH$_2$—COOH or from 1 to 4 R represent —CH$_2$—COOH or —CH$_2$—CH(CH$_3$)—COOH or —CH$_2$—CH(C$_2$H$_5$)—COOH, is reacted with a sulfonating agent and wherein the amount of said sulfonating agent is such that said reaction converts at least two H per glucopyranose unit into —SO$_3$H groups.

The starting material for the above particular embodiment is commercially available or can be made by techniques well known in the art. A carboxymethylated β-cyclodextrin with a degree of substitution of 3.5 is commercially available from Cyclolab Ltd. (Hungary). A carboxymethylated β-cyclodextrin with a degree of substitution of 3.6 is described by Jin & Li in *J. Chromatogr. B* (1998) 708:265. The skilled person understands that a degree of substitution value which is not an integer is an average value which is representative of a mixture of molecules. For instance a carboxymethylated β-cyclodextrin with a degree of substitution of 3.5 may represent a 50/50 mixture of carboxymethylated β-cyclodextrin with 3 carboxymethyl substituents and carboxymethylated β-cyclodextrin with 4 carboxymethyl substituents.

A carboxyethylated β-cyclodextrin with a degree of substitution of 3 is commercially available from Cyclolab Ltd. (Hungary). Carboxyethylated β-cyclodextrins with various degrees of substitution may be produced by reacting β-cyclodextrin with acrylamide under Michael addition conditions such as, but not limited to the procedure described at pages 513-516 of the Proceedings of the $9^{th}$ International Symposium on Cyclodextrins (1998). Carboxyethylated β-cyclodextrins with a degree of substitution from 2.2 to about 3.0, i.e. wherein an average from 2.2 to 3.0 R groups represent —$CH_2$—$CH_2$—COOH in the above structural formula, may also be obtained by routine optimization of said Michael addition conditions.

In a similar way, carboxypropylated (R=—$CH_2$—CH($CH_3$)—COOH) and carboxybutylated (R=—$CH_2$—CH($C_2H_5$)—COOH) β-cyclodextrins with various degrees of substitution may be produced by reacting β-cyclodextrin under Michael addition conditions with methacrylamide or ethacrylamide respectively.

The amount of acrylamide, methacrylamide or ethacrylamide to be used may be a molar excess (e.g. a molar ratio within a range from 1 to 100) with respect to the amount of β-cyclodextrin. The reaction can be carried out under cooling or heating conditions, for instance at a temperature within a range of 40° C. to 95° C., and optionally in the presence of a suitable solvent.

The reaction of carboxyethyl-β-cyclodextrin with a sulfonating agent may be carried out in a suitable solvent. As the sulfonating agent, there may suitably be used, for example, a sulphur trioxide complex, such as sulphur trioxide-pyridine complex, sulphur trioxide-trialkylamine complex, sulphur trioxide-dioxane complex, sulphur trioxide dimethylformamide complex and the like, anhydrous sulphuric acid, concentrated sulphuric acid, chlorosulfonic acid, and so on.

The amount of the sulfonating agent to be used may be in excess of the amount of the carboxyalkylated-β-cyclodextrin, e.g. the carboxyethyl-β-cyclodextrin. For example, where a sulphur trioxide-pyridine complex or a sulphur trioxide-trialkylamine complex is used as a sulfonating agent, the amount thereof to be used may preferably be from 1 to 10 molar equivalents, especially from 2 to 5 molar equivalents, relatively to the amount of carboxyalkylated-β-cyclodextrin, e.g. carboxyethyl-β-cyclodextrin.

As a solvent for the sulfonylation reaction, there may preferably be used for example a tertiary amine such as pyridine, picoline, lutidine, N,N-dimethylformamide, formamide, hexamethylenephosphoryltriamide, chloroform, benzene, toluene, xylene, water, alcohols or a mixture of these solvents in any suitable proportions, liquid sulphur dioxide and so on. The sulfonylation reaction can be carried out under cooling or heating conditions and may preferably be carried out under heating, preferably at a temperature within a range of 40° C. to 100° C.

More specifically, and depending upon the sulfonylation reaction conditions (such as, but not limited to, temperature, reaction time, etc), the carboxyalkylated β-cyclodextrin polysulfate compounds represented by the structural formula (I) may be obtained as a mixture of compounds, e.g. in which either sixteen $SO_3H$ groups or seventeen $SO_3H$ groups or eighteen $SO_3H$ groups are present.

After completion of the sulfonylation reaction, the reaction product, which is a β-cyclodextrin compound represented by the structural formula (I) in its acidic form, can be isolated and purified or can be used as such for further conversion into a pharmaceutically acceptable salt. For example, the crude product obtained from the sulfonylation reaction can be treated with an alkali metal compound such as, but not limited to, sodium acetate to produce the corresponding alkali metal, e.g. sodium salt. If desired to achieve a pharmaceutical grade with high purity, the latter may then be submitted to further purification by washing with methanol and/or treatment with activated charcoal.

In another aspect of this invention, it has been found that carboxyalkylated β-cyclodextrin polysulfate compounds, including pharmaceutically acceptable salts thereof and/or solvates thereof, such as represented by the structural formula (I), including any one of the particular embodiments described above, especially those with an average of three 2-carboxyethyl chains (i.e. meeting the proviso that three R represent —$CH_2$—$CH_2$—COOH) activated significantly fewer platelets in comparison with heparin and other polysulfated β-cyclodextrin derivatives in an in vitro model of HIT, indicating that the compounds of the present invention, in particular CE-CDPS, exhibit no cross-reactivity with the heparin- and platelet factor IV—complex reactive antibodies.

Thus, in another aspect, the present invention relates to a pharmaceutical composition comprising a carboxyalkylated β-cyclodextrin polysulfate compound represented by the structural formula (I), including pharmaceutically acceptable salts thereof and/or solvates thereof, and including any one of the particular embodiments described above, in combination with one or more non-toxic, pharmaceutically acceptable excipients.

By virtue of their biochemical and pharmaceutical activity the novel carboxyalkylated β-cyclodextrin polysulfate compounds of the present invention constitute very advantageous medicines. Their low toxicity is entirely compatible with this use. They are also very stable and are thus particularly suitable for constituting the or an active principle (ingredient) of pharmaceutical compositions.

Preferably the pharmaceutical composition of the present invention comprises carboxyalkylated β-cyclodextrin polysulfate compounds represented by the structural formula (I), the glucopyranose unit of which shows an average degree of sulfation in the range of 1.00 to 2.57, preferably in the range of 1.43 to 2.57, more preferably in the range of 2.28 to 2.57, most preferably the degree of sulfation is equal to 2,57.

As is well known to the skilled person, the degree of sulfation, or degree of substitution (DS), of the β-cyclodextrin glucopyranose unit can be calculated as follows:

$$DS = [\% \, S^* m_a(C) / \% \, C^* m_a(S)]^* \text{ total number of C,}$$

wherein $m_a$ is the atomic mass.

In each dosage unit of the pharmaceutical composition of the present invention, the active principle, i.e. the carboxyalkylated β-cyclodextrin polysulfate compound represented by the structural formula (I), including pharmaceutically acceptable salts thereof and/or solvates thereof, and including any one of the particular embodiments described above, is preferably present in a therapeutically effective amount, i.e. an amount appropriately adjusted according to the frequency and type of administration envisaged, for example tablets, gelatine capsules and the like, sachets, vials, syrups and the like, drops, transdermal or transmucous patches. Preferably such a dosage unit contains from 10 to 5,000 mg, preferably 20 to 500 mg, more preferably 25 to 250 mg, of active principle.

The compounds according to the present invention can also be used, for instance in a pharmaceutical composition, in combination with one or more other active principles (ingredients) being useful for any one of the desired therapies specified below. Suitable examples of such active principles (ingredients) include, but are not limited to, anti-thrombotic agents, anti-coagulants, anti-inflammatory agents, cell products and anti-platelet-aggregating agents, for example dipyridamole, aspirin, ticlopidine, clopidogrel or antagonists of the glycoprotein IIb/IIIa-complex. Another example of a suitable active ingredient is a chemokine capable of promoting cartilage formation in vivo, such as CXCL6, or CXCL6-expressing cells such as disclosed in WO 2005/014026.

The term "cell products" as used herein with respect to an active ingredient to be combined with a novel carboxyalkylated β-cyclodextrin polysulfate compound of this invention includes:
  chondrogenic cells, i.e. cells capable of producing stable hyaline cartilage, and
  precursor cells of chondrogenic cells, i.e. a precursor cell capable of undergoing differentiation into a chondrogenic cell such as previously defined; they include stem cells, which can be obtained from different tissues including bone-marrow or umbellical cord; a particularly suitable embodiment consists of skeletal precursor cells such as those obtained from the synovial membrane which are capable of differentiating into cartilage producing cells, such as described in WO 01/25402.

The pharmaceutical compositions according to the present invention may be formulated for administration to mammals, including human beings, for the treatment of any one of the diseases specified below.

Preferably a pharmaceutical composition of the present invention, whether including a novel carboxyalkylated β-cyclodextrin polysulfate compound alone or in combination with another active ingredient as specified hereinabove, may be used for the treatment and/or prophylaxis of degenerative joint diseases, preferably osteoarthritis, as well as articular rheumatism, arthrosis or degenerative arthritis, or for the treatment of heparin-induced thrombocytopenia, or for cartilage repair or connective tissue repair.

The pharmaceutical compositions of the present invention are particularly suitable for the treatment of the heparin-induced thrombocytopenia syndrome without inducing platelet activation or thrombosis in the presence of heparin- and platelet factor IV-complex reactive antibodies.

The pharmaceutical compositions of the present invention may be advantageously obtained in various forms, such as, for example, injectable or drinkable solutions, sugar-coated tablets, ordinary tablets or gelatine capsules. Injectable solutions are the preferred pharmaceutical forms. The suitable dosage can vary within a wide range depending on the base patient's age, weight and state of health, the nature and severity of the disease, as well as on the route of administration. One suitable therapeutic regime comprises the administration of one or more dosage units of about 20 mg to about 500 mg per day, intramuscularly or sub-cutaneously either continuously or discontinuously at more or less regular time intervals.

Another embodiment of the present invention relates to compositions containing a carboxyalkylated β-cyclodextrin polysulfate compound represented by the structural formula (I), including pharmaceutically acceptable salts thereof and/or solvates thereof, and including any one of the particular embodiments described above, combined with another active principle or ingredient for administration via the digestive or parenteral route.

In the pharmaceutical compositions of the present invention for oral, sublingual, subcutaneous, intramuscular, intravenous, transdermal, transmucous, local or rectal administration, the active principle can be administered in unit forms of administration, mixed with standard pharmaceutical carriers or excipients, to animals or human beings. The appropriate unit forms of administration comprise:
  oral forms, such as tablets, gelatine capsules, powders, granules and oral suspensions or solutions,
  sublingual and buccal forms of administration,
  subcutaneous, intramuscular, intravenous, intranasal or intraocular forms of administration, and
  rectal forms of administration.

When a solid composition in tablet form is prepared, the main active ingredient may be mixed with one or more pharmaceutically acceptable vehicles or excipients such as, but not limited to, gelatine, starch, lactose, magnesium stearate, talc, Gum Arabic or the like. The tablets can be coated with sucrose or other suitable materials, or, alternatively, they can be treated such that they have sustained or delayed activity and such that they release a predetermined amount of active principle continuously. A preparation in gelatine capsules is obtained by mixing the active ingredient with a diluent and by pouring the mixture obtained into soft or hard gelatine capsules. The water-dispersible powders or granules can contain the active ingredient mixed with dispersing agents or wetting agents, or with suspension agents, such as polyvinylpyrrolidone, as well as with sweeteners or flavour enhancers.

For rectal administration, use is made of suppositories which are prepared with binders which melt at the rectal temperature, for example cocoa butter or polyethylene-glycols.

For parenteral, intranasal or intraocular administration, aqueous suspensions, isotonic saline solutions or sterile injectable solutions which contain pharmacologically compatible dispersing agents and/or wetting agents, for example propylene glycol or polybutylene glycol are used.

For transmucous administration, the active principle can be formulated in the presence of the promoter such as bile salt, hydrophilic polymer, such as, for example, hydroxypropylcellulose, hydroxypropylmethylcellulose, hydroxyethyl-cellulose, ethylcellulose, carboxymethylcellulose, dextran, polyvinylpyrolidinone, pectins, starch, gelatine, casein, acrylic acids, acrylic esters and copolymers thereof, vinyl polymers or copolymers, vinyl alcohols, alkoxy polymers, polyethylene oxide polymers, polyethers or mixtures thereof.

The active principle can also be formulated in the form of microcapsules, optionally with one or more carriers or additives.

For oral administration, fine powders or granules may contain diluting, dispersing and/or surface active agents, and may be presented in water or in a syrup, in capsules or sachets in the dry state, or in a non-aqueous solution or suspensions wherein suspending agents may be included in tablets wherein binders and lubricants may be included, or in a suspension in water or a syrup. Where desirable or necessary, flavouring, preserving, suspending, sickening or emulsifying agents may be included. Tablets and granules are preferred oral administration forms, and these may be coated. To enhance oral penetration and gastrointestinal absorption, the carboxyalkylated β-cyclodextrin polysulfate compounds represented by the structural formula (I) can be formulated with mixtures of olive oil, bile salts or sodium N[8-(2-hydroxybenzyl-benzoyl)amino]caprylate.

EXAMPLE 1

Sulfation of Carboxyethyl-β-Cyclodextrin

Pyridine sulfonate (sulfur trioxide pyridine complex) was heated in a water bath to 70-80° C. Pyridine sulfonate (1000 mL) was added to a mechanically stirred vessel with a side arm, and maintained at 80° C. with a water bath. A carboxyethyl-β-cyclodextrin with a degree of substitution of 3 (100 g)

from Cyclolab Ltd. (Hungary) was added slowly with rapid stirring. The mixture was maintained at 80° C. with stirring for 2.5 hours, then water (500 mL) was added.

EXAMPLE 2

Preparation of the Sodium Salt of Carboxyethyl-β-Cyclodextrin Sulfate

The reaction mixture resulting from example 1 was poured with rapid stirring into methanol (7500 mL) containing sodium acetate (750 g). The precipitate was isolated by filtration using a Buchner funnel, washed with methanol (2000 mL), air dried, then dried under vacuum. The precipitate (sodium salt of carboxyethyl-β-cyclodextrin sulfate) was then dissolved in water (1000 mL), and the resulting aqueous solution was analyzed for free sulfate content, and $BaCl_2$ dissolved in hot water was added to precipitate barium sulfate. The precipitate was allowed to settle, then removed by centrifugation. Five volumes of methanol was added to the supernatant to precipitate the product and this was isolated by Buchner funnel, washed with methanol and dried under vacuum.

EXAMPLE 3

Activated Charcoal Treatment of a Carboxyethyl Cyclodextrin Polysulfate sodium salt 2-carboxyethyl-β-cyclodextrin polysulfate sodium salt (hereinafter referred as CE-CDPS) from example 2 was dissolved at the rate of 300 mg/mL in water. Activated charcoal (10 g) was added for each 100 g of the cyclodextrin polysulfate sodium salt. The mixture was stirred for 30 minutes at room temperature, and filtered several times to remove charcoal including the use of a final 0.2 μm filter membrane. The filtered cyclodextrin compound solution was slowly added into five volumes of stirred methanol. The mixture was stirred for 10 minutes. The resulting product was isolated by filtration, washed with methanol, and dried under vacuum. Its elemental analysis data are provided in table 1.

EXAMPLE 4

Comparative Elemental Analysis of β-Cyclodextrin Derivatives 2,3,6-tri-O-methyl-β-cyclodextrin (ME-CD) and 2,6-di-O-methyl-3-sulfate-β-cyclodextrin (ME-CD-3-S) were purchased from Cyclolab Ltd (Hungary). 2,3-di-O-methyl-6-sulfate-β-cyclodextrin (ME-CD-6-S was available from Regis Technologies Inc. (Morton Grove, Ill., USA). 2-hydroxypropyl-β-cyclodextrin (HP-CDPS) was available from Sigma Chemical Company, and sulfated 6-monodeoxy-6-monoamino-β-cyclodextrin (MA-CDPS) from Cyclolab Ltd. Their elemental analysis data are provided in table 1 for comparative purpose with the data of the purified 2-carboxyethyl-β-cyclodextrin polysulfate sodium salt of example 3.

TABLE 1 elemental analysis of different β-cyclodextrin derivatives

| β-cyclodextrin | Abbreviation | Elemental analysis | | | | S-Substitution | DS/glucopyranose |
|---|---|---|---|---|---|---|---|
| | | % C | % H | % N | % S | | |
| 2,3,6-tri-O-methyl-β-cyclodextrin | ME-CD | | | | | | 0.00 |
| Heptakis (2,6-O-methyl)-β-cyclodextrin heptasulfate | ME-CD-3-S | | | | | | 1.00 |
| heptakis (2,3-dimethyl-6-sulfato)-β-cyclodextrin | ME-CD-6-S | 28.66 | 4.50 | <0.05 | 9.77 | 7.12 | 1.02 |
| Sulfated 6-monoamino-6-monodeoxy β-cyclodextrin | MA-CDPS | 16.11 | 2.78 | .47 | 16.34 | 15.96 | 2.28 |
| Sulfated (2-carboxyethyl)-β-cyclodextrin | CE-CDPS | 16.80 | 2.63 | <0.05 | 15.33 | 17.34 | 2.47 |
| Sulfated (2-hydroxypropyl)-β-cyclodextrin | HP-CDPS | 18.91 | 3.28 | <0.05 | 16.40 | 20.48 | 2.92 |
| β-cyclodextrin polysulfate | CDPS | 17.28 | 2.86 | <0.05 | 16.94 | 15.41 | 2.21 |

EXAMPLE 5

Isolation of Articular Chondrocytes

Human articular chondrocytes were isolated as described in *J. Tissue Culture Methods* (1993) 15:139-146). Briefly, human articular cartilage was obtained at total knee replacement surgery from femoral condyles and the tibial plateau of 15 different donors. None of them had received corticosteroids or cytostatic drugs. Both visually intact and fibrillated OA cartilage samples were harvested separately and only OA cartilage was used for cell culture. The cartilage samples were diced into small fragments and the chondrocytes were isolated by sequential enzymatic digestion (hyaluronidase, pronase and collagenase) of the extracellular matrix (ECM) as described in *Osteoarthritis Cartilage* (2001) 9:73-84. Isolated cells were then centrifuged for 10 minutes at 1500 rpm, washed three times in Dulbecco's Modified Eagle's Medium (DMEM) with 10% (v/v) fetal calf serum, and counted with trypan blue to exclude dead cells. More than 90% of the cells were viable after isolation.

EXAMPLE 6

Chondrocyte Cultures in Alginate Gel

Chondrocytes were cultured in alginate beads, to maintain their differentiated phenotype. The cultures were prepared as described in *Connect Tissue Res*. (1989) 19:277-297. Chondrocytes suspended in one volume of double-concentrated Hank's Balanced Salts Solution (HBSS, commercially available from Gibco) without calcium and magnesium were carefully mixed with an equal volume of 2% (w/v) autoclaved alginate (low-viscosity alginate from *Macrocystis pyrifera*, commercially available from Sigma) in HBSS. The final cell concentration was $5 \times 10^6$ chondrocytes per ml in 1% alginate. The chondrocyte/alginate suspension was then slowly dripped through a 23-gauge needle into a 102 mM calcium chloride solution. The beads were allowed to polymerize for 10 minutes at room temperature. After removal of the calcium chloride, the beads were washed three times with 0.15 M sodium chloride. Alginate beads were cultured in 12-well plates with $10^6$ cells per culture (each well containing 20 alginate beads; ±50,000 chondrocytes per bead) in 3 ml DMEM supplemented with 10% FCS and 50 mg ascorbate/ml at 37° C. under 5% $CO_2$. Nutrient medium was replaced twice weekly. It is known that ECM metabolism by chondrocytes reaches steady state after 1 week in this alginate culture system.

EXAMPLE 7

Chondrocyte Treatment with Sulfated β-Cyclodextrins in Vitro

Cartilage cells obtained from osteoarthritic (OA) cartilage of 15 donors were used to evaluate the effect of the different β-cyclodextrins polysulfates on the synthesis and accumulation of ECM aggrecan. At day 5 of culture, the OA chondrocytes of each donor were exposed to 5 µg/ml of respectively ME-CD, ME-CD-3-S, ME-CD-6-S, MA-CDPS, HP-CDPS, CE-CDPS and CDPS (as defined in examples 3-4 and characterised in table 1). After 5 additional culture days, media were collected and stored at −20° C. for further analysis of IL-6 concentrations. The cells were separated from their alginate coat by dissolving the alginate with 3 ml of 55 mM trisodium citrate dehydrate pH 6.8, 0.15 M NaCl at 25° C. for 10 minutes. The resulting suspension was centrifuged at 1,500 rpm for 10 minutes. to separate the supernatant containing the constituents of the interterritorial matrix from the cells with their cell associated matrix (CAM). The aggrecan content in the inter-territorial matrix was assayed by ELISA (Biosource, Belgium) according to the manufacturer's instructions. All experiments were performed in triplicate.

EXAMPLE 8

β-Cyclodextrin Polysulfates and Blood Coagulation Activities

MA-CDPS, HP-CDPS, CE-CDPS and CDPS (as defined in examples 3-4 and characterised in table 1) were prepared as buffered solutions at various concentrations. The polysaccharides were incubated with normal pooled plasma prepared out of 40 healthy volunteers and analyzed for their effects on activated partial thromboplastin time (aPTT), prothrombin time (PT) and fibrinogen levels on a STA Compact® coagulation analyzer (available from Diagnostica Stago, Asnieres, France) according to the manufacturers instructions.

EXAMPLE 9

β-Cyclodextrin Polysulfates and Heparin-Induced Thrombocytopenia

The activation of healthy donor thrombocytes by HIT patient anti-heparin/PF4 antibodies in the presence of heparin and the differently sulfated forms of β-cyclodextrin was tested. Plasma of patients that experienced heparin-induced thromboembolic (HIT) accidents following the administration of heparin and that showed anti-heparin/PF4 antibodies (HIT Ab) on immunological and flow cytometric tests were selected for these assays. The expression of CD62p by the activated platelets was assayed by means of flow cytometry with a FC500 analyzer (available from Beckman Coulter, Belgium). Platelet-rich plasma solution (PRP) was prepared by slow centrifugation (10 minutes at 180 g) of fresh citrate anti-coagulated blood (1:9 v/v, 0.129 mol/L or 3.8% trisodium citrate buffer), obtained from normal donors. HIT Ab positive plasma samples from patients and HIT Ab negative control plasma from healthy donors were prepared by double centrifugation (15 minutes at 2230 rpm) of fresh citrate anti-coagulated blood. 70 µl of PRP was incubated with 20 µL of HIT Ab containing plasma optionally in the presence of heparin (0.3 IU/ml) or the relevant β-cyclodextrin derivative (5 µg/ml). Experiments with each HIT Ab positive plasma sample were repeated independently using thrombocytes of 2 donors (A and B), to avoid the possibility of non-reactive platelets.

Following the initial 40 minutes incubation step, 5 µl of the platelets solution was transferred to a fresh tube with 85 µL phosphate buffered saline (PBS) containing 1% bovine serum albumin (BSA) and 0.1% Na-azide, 5 µl (0.25 µg) monoclonal anti-CD41 antibodies (Ab) (phycoerythrin-Texas Red Energy coupled dye (ECD)-conjugated, Beckman Coulter) and 5 µl (0.125 µg) of anti-CD62p Ab (phycoerythrin (PE)-conjugated, Beckman Coulter). CD41 (Glycoprotein IIb) is a selective marker of platelets and platelet precursors. CD62p is a constituent of alpha granules and is released to the platelet surface on activation.

After 20 minutes of incubation at room temperature, the total volume of the platelet suspension was adjusted to 600 µL buffered solution and evaluated without delay by flow cytometry. 20,000 events per sample were analysed and the platelet populations were gated by side scatter characteristics and the platelet marker CD41. Activated platelets ($CD62p^+$) were distinguished from resting platelets by the CD62p-PE expression (as shown in FIG. 3). The fraction of activated platelets among the total platelet population was determined and relative CD62p ratios to the internal controls were calculated. [ratio: % $CD62p^+$ (0.3 IU Heparine or 5 µg/ml β-cyclodextrin derivative)/% $CD62p^+$ (0 IU Heparine or 0 µg/ml β-cyclodextrin derivative)]. Test results for the heparin treated platelets were evaluated by the scoring system described in *Thromb. Haemost.* (1999) 82:1255-1259. Control tests were scored positive when the calculated ratios of at least 2 donors were more then 2, based on previously obtained results with normal individuals. To evaluate the potential of the different β-cyclodextrin derivatives to induce platelet activation, both the percentages and ratios of $CD62p^+$ platelets after incubation with the respective β-cyclodextrin were statistically compared to the percentage and the ratio of $CD62p^+$ platelets after heparin incubation.

EXAMPLE 10

Induction of Experimental Osteoarthritis

Knee osteoarthritis was induced by injecting the right knees of adult (10 weeks) C57Bl/6 male mice with 10 µl of a 2 U/µl collagenase type VII (Sigma C-9572, available from Sigma-Aldrich Belgium) solution. The left knee of these animals was injected with 10 µl PBS and served as a control. Two groups of each 8 mice were randomized on weight, the first group was injected subcutaneously once weekly, with 1 mg/kg of the CE-CDPS of example 3, the second group was treated with saline. Treatment was initiated three days after the mice received their intra-articular injection. The animals were fed a standard diet with tap water ad libitum and their weight was recorded twice a week. The mice were sacrificed three weeks after induction of knee osteoarthritis and the liver, kidneys and knee joints were fixed immediately in 2% neutral buffered paraformaldehyde (Fluka 76240, available from Sigma-Aldrich Belgium).

EXAMPLE 11

Histopathology

After fixation, knee joints were decalcified in 0.5 M EDTA in PBS and embedded in paraffin. 5μ tissue sections were cut and stained with haematoxylin and eosin for an analysis of the general morphology or with safranin-O for an assessment of proteoglycan content. Each 100 μm, 3 sections of the joint were evaluated.

Stained slides were submitted for evaluation. The following parameters were evaluated: synovial inflammation, fibrosis, osteophytes and erosion of cartilage. Synovial inflammation was graded from 0 to +3 as follows: 0 no changes from normal; +1 mild changes; +2 moderate changes; and +3 severe changes.

Fibrosis was scored as follows: 0 no changes from normal; +1 fibrosis without metaplasia; +2 fibrosis associated with chondroplasia; +3 fibrosis associated with metaplastic bone. Osteophytes were graded from 0 to +4 referring to the amount of osteophytes observed, with a maximum score of 1 per compartment.

Cartilage erosion was graded from 0 to +3 as follows: 0 no changes from normal; +1 only superficial erosion; +2 loss of proteoglycan in one compartment; and +3 loss of proteoglycan in different compartments. In this scoring system the femoral/tibial junction as a whole was taken in consideration by 2 independent investigators.

EXAMPLE 12

Statistical Analysis

To study the impact of the changes in the chondrocyte cultures after cyclodextrin polysulfate treatment, mean IL-6 and aggrecan concentrations were calculated from triplicate chondrocyte cultures of each donor. Wilcoxon signed rank tests were used to test significance of differences between untreated controls and cultures after exposure to the different cyclodextrin polysulfates. Cross-reactivity with heparin of the polysaccharides on in vitro induced platelet activation was analysed by Wilcoxon signed rank test. Evolution of mouse weight over time was analysed by longitudinal data analysis methods, more specific by area under the curve and mixed model analysis. The histological scores were compared by Mann-Whitney tests. Significance levels for all tests were set at p <0.05.

EXAMPLE 13

Effects on Aggrecan Production and Inhibition of IL-6 Release by Sulfated β-Cyclodextrins Non-sulfated ME-CD failed to promote aggrecan synthesis or to affect IL-6 release and was used as a control in the experiments on isolated chondrocytes. Furthermore, the monosulfated cyclodextrins ME-CD-3-S and ME-CD-6-S also failed to affect chondrocyte's aggrecan synthesis and IL-6 secretion. Bi-sulfated (CDPS, MA-CDPS) and trisulfated β-cyclodextrins (HP-CDPS, CE-CDPS) however significantly enhanced chondrocyte aggrecan synthesis by an average of 50% to 70% (as shown in FIG. 1A). These highly sulfated β-cyclodextrins also significantly repressed chondrocyte IL-6 secretion (as shown in FIG. 1B).

EXAMPLE 14

-βCyclodextrin Effects on Blood Coagulation Activities

With increasing concentrations, the aPTT values (s) stagnated up to a concentration of 5 μg/ml for all the CDPS derivatives studied. Above 50 μg/ml no clot formed for the derivatives studied in the observation time of the experiment (as shown in FIG. 2a). The same tendency was observed for PT values (s), except for the far more limited increase in pro-thrombin time for concentrations above 50 μg/ml (as shown in FIG. 2b). Minor decreases were observed in fibrinogen concentrations (mg/ml) after incubation with 50 or 100 μg/ml of MA-CDPS, HP-CDPS, CE-CDPS or CDPS, respectively (as shown in FIG. 2c). No influence on the blood coagulation cascade could thus be detected at concentrations which highlighted a chondroprotective effect in vitro.

EXAMPLE 15

Induction of Platelet Activation

All HIT Ab positive plasma samples showed platelet heparin activation ratios % $CD62p^+$ (0.3 IU heparin)/% $CD62p^+$ (0 IU heparin) above 2 for the two donors, indicating an activation of platelets by heparin/PF4 antibodies. Platelets were not activated by heparin or any of the β-cyclodextrin polysulfate derivatives in the absence of patient's HIT Ab.

Immunological cross-reactivity between heparin and some of the polysulfated β-cyclodextrins became evident as HP-CDPS, MA-CDPS and CDPS induced platelet activation in the presence of the plasma samples of the individuals that had developed HIT Ab upon previous exposure to heparin (as shown in FIG. 3). Paired analysis of both ratios and percentages of CD62p positive cells confirmed a significant difference (p=0.017 for percentages and p=0.012 for ratios) between heparin and CE-CDPS incubated platelets, indicating that CE-CDPS exhibited no cross-reactivity with the heparin/PF4 antibodies (Table 2). Moreover, the p-values calculated from the paired analysis of ratios and percentages of activated platelets between CE-CDPS and each of the other analysed cyclodextrins were lower than 0.05.

EXAMPLE 16

Effects of Ce-Cdps on Experimental Osteoarthritis of the Knee

Since CE-CDPS had the best safety profile when the in vitro tests for HIT were considered, this compound was used in the mouse experiment osteoarthritis model. CE-CDPS treatment did not affect the weight of the animals. There was no difference in the body weight between the treatment and the control group throughout the study.

The intra-articular administration of collagenase in the mouse knee joint causes a weakening of the ligament, leading to joint laxity. As a consequence of mechanical instability and presumably a concomitant release of a number of antigenic neo-epitopes, these mice developed OA lesions and a severe synovial inflammatory reaction. In comparison to the healthy control knees, the OA knees of the CE-CDPS- as well as the PBS-treated mice, showed a severe invasion of inflammatory cells in the synovium with marked synovial pannus formation. Osteophyte formation was also prominent in these OA joints. Synovial inflammation, pannus formation and osteophyte growth were not inhibited by the treatment. In contrast, overall cartilage damage was reduced in the CE-CDPS-treated mice as Safranine O staining of both the tibial plateau and the femoral condyles in knees of treated mice was more conserved as compared to control PBS-treated knees (as shown in FIG. 4).

TABLE 2 platelet activation by heparin and polysulfated β-cyclodextrin derivatives

|  |  | pat1 | | pat2 | | pat3 | | pat4 | | p-values | | | |
|---|---|---|---|---|---|---|---|---|---|---|---|---|---|
|  |  | dA | dB | dA | dB | dA | dB | dA | dB | heparin | MA-CDPS | CE-CDPS | HP-CDPS |
| heparin | ΔCD62p+ % | 45.5 | 14.3 | 45.6 | 15.1 | 60.3 | 42.3 | 34.8 | 56.4 | ref | | | |
|  | ratio | 4.2 | 2.2 | 2.8 | 3.9 | 4.3 | 8.2 | 2.7 | 2.8 | ref | | | |
| MA-CDPS | ΔCD62p+ % | 74.8 | 69.9 | 9.6 | 17.4 | 16.7 | 32.6 | 51.1 | 63.6 | 0.779 | ref | | |
|  | ratio | 5.2 | 5.5 | 1.4 | 3.5 | 1.9 | 8.2 | 3.5 | 3.1 | 0.779 | ref | | |
| CE-CDPS | ΔCD62p+ % | 13.9 | 14.4 | 2.4 | 1.1 | 7.9 | 10.2 | 22.9 | 45.0 | 0.017 | 0.012 | ref | |
|  | ratio | 1.8 | 2.2 | 1.1 | 1.2 | 1.4 | 2.7 | 2.2 | 2.4 | 0.012 | 0.012 | ref | |
| HP-CDPS | ΔCD62p+ % | 67.6 | 53.0 | 0.1 | 1.2 | 23.3 | 17.1 | 63.2 | 60.7 | 0.779 | 0.123 | 0.025 | ref |
|  | ratio | 4.9 | 5.1 | 1.0 | 1.1 | 2.1 | 4.7 | 4.6 | 2.8 | 0.484 | 0.123 | 0.036 | ref |
| CDPS | ΔCD62p+ % | 76.1 | 73.1 | 27.5 | −2.8 | 42.7 | 34.1 | 63.5 | 58.1 | 0.484 | 0.327 | 0.017 | 0.093 |
|  | ratio | 5.8 | 6.5 | — | 0.7 | 2.5 | 7.0 | 4.4 | 2.5 | 0.889 | 0.889 | 0.025 | 0.123 |

Platelets from 2 different donors (dA and dB) were incubated with plasma samples containing HIT ab from 4 patients (pat 1, 2, 3, 4) and with the different sulphated polysaccharides. ΔCD62p+ %: Percentage increases in CD62p positive platelets; ratio: % CD62p+ (0.3 IU Heparine or 5 μg/ml sulpated polysaccharide)/% CD62p+ (0 IU Heparine or 0 μg/ml sulphated polysaccharide).

Figure 1:
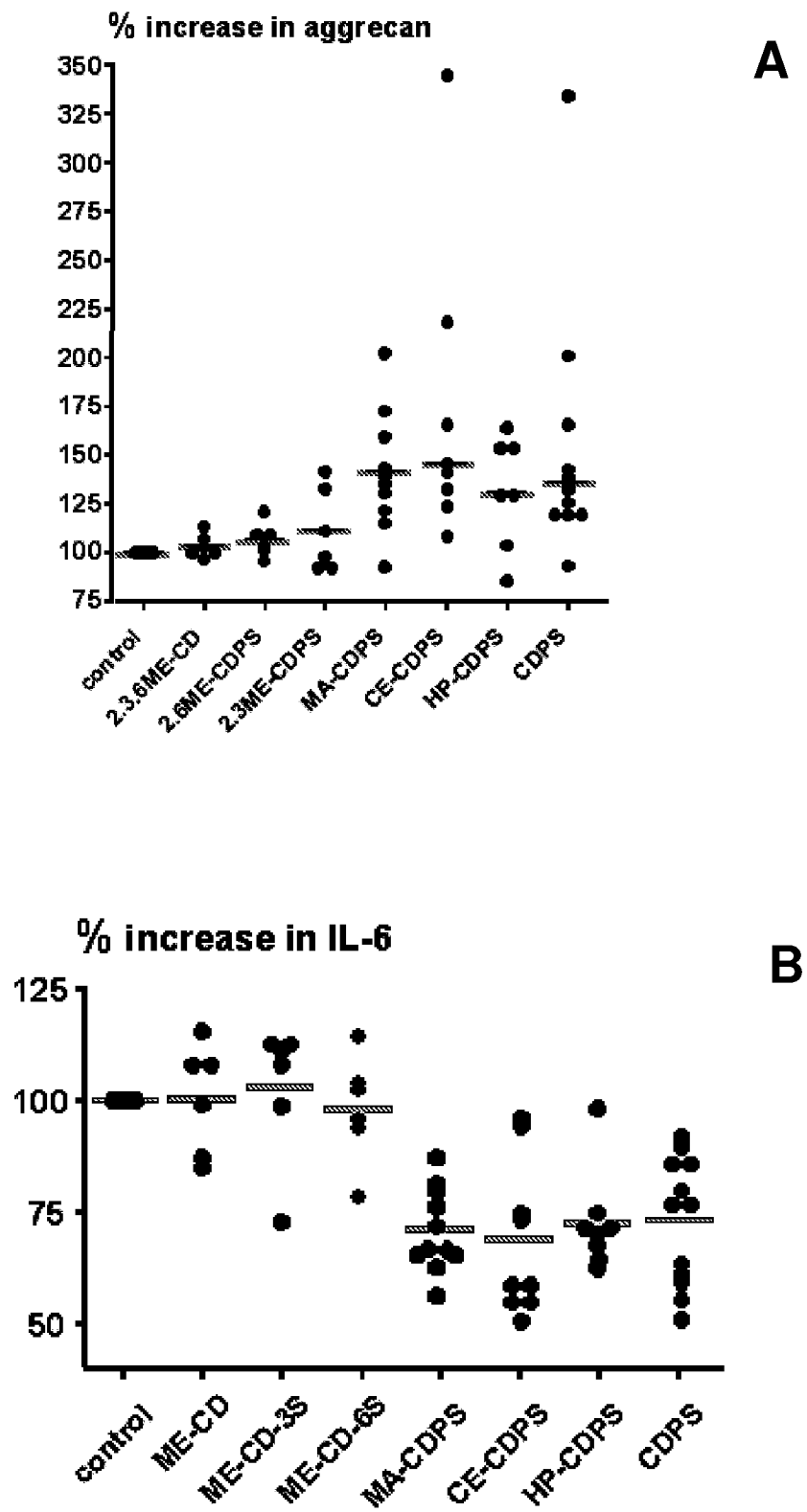
FIG. 1A shows percentage changes in aggrecan production by osteoarthritic chondrocytes treated with β-cyclodextrin polysulfate derivatives. Dots represent mean values of triplicates cultures of one patient. Bars represent the overall average.
FIG. 1B shows percentage changes in IL-6 release by OA chondrocytes treated with β-cyclodextrin polysulfate derivatives. Dots represent mean values of triplicates cultures of one patient. Bars represent the overall average.
Figure 2:
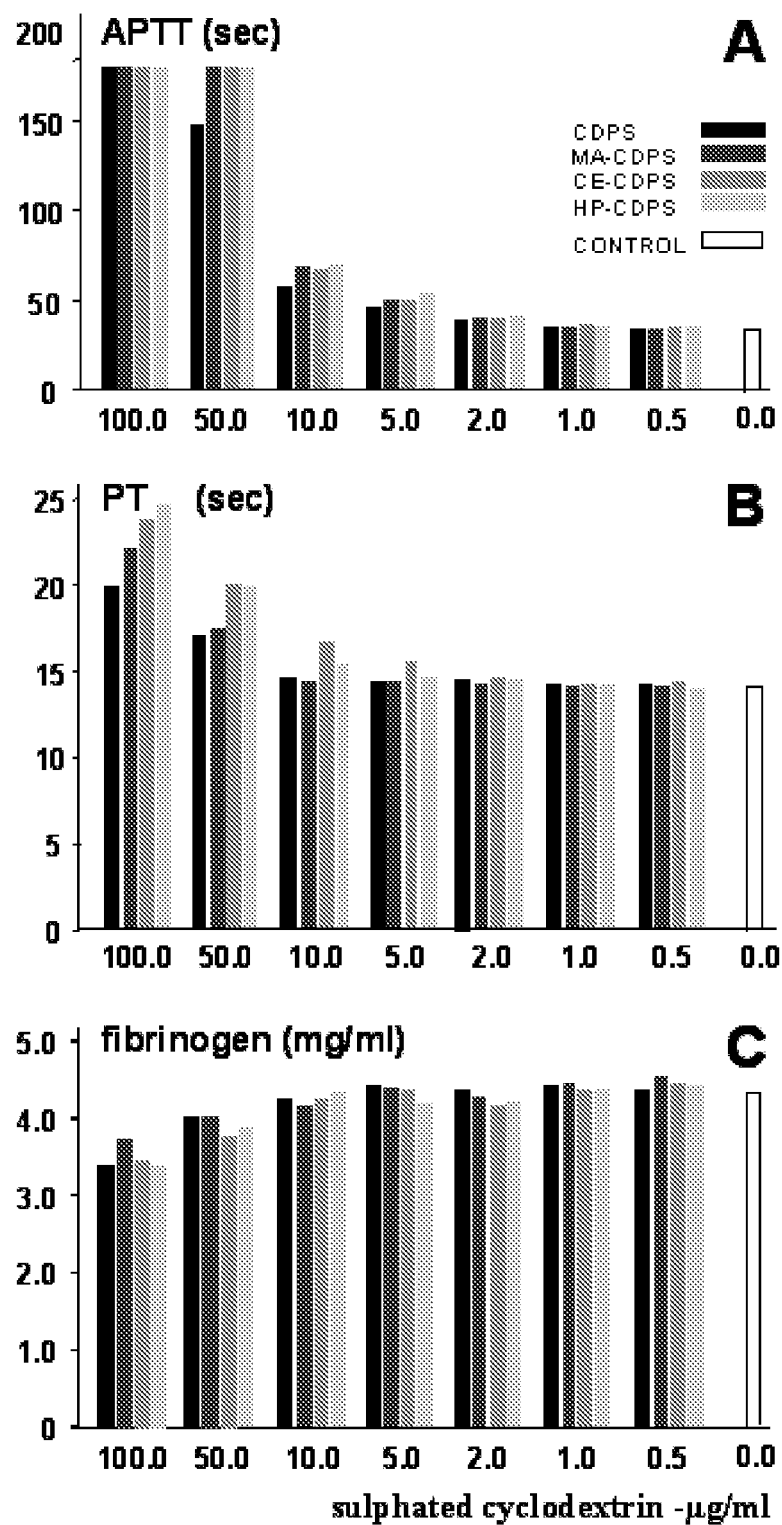
FIG. 2 shows the effects of β-cyclodextrin polysulfate derivatives on variables of plasma coagulation activity. ordinate: aPTT (seconds), PT (seconds), fibrinogen (mg/ml); abscissa: sulfated cyclodextrins (μg/ml).
Figure 3:
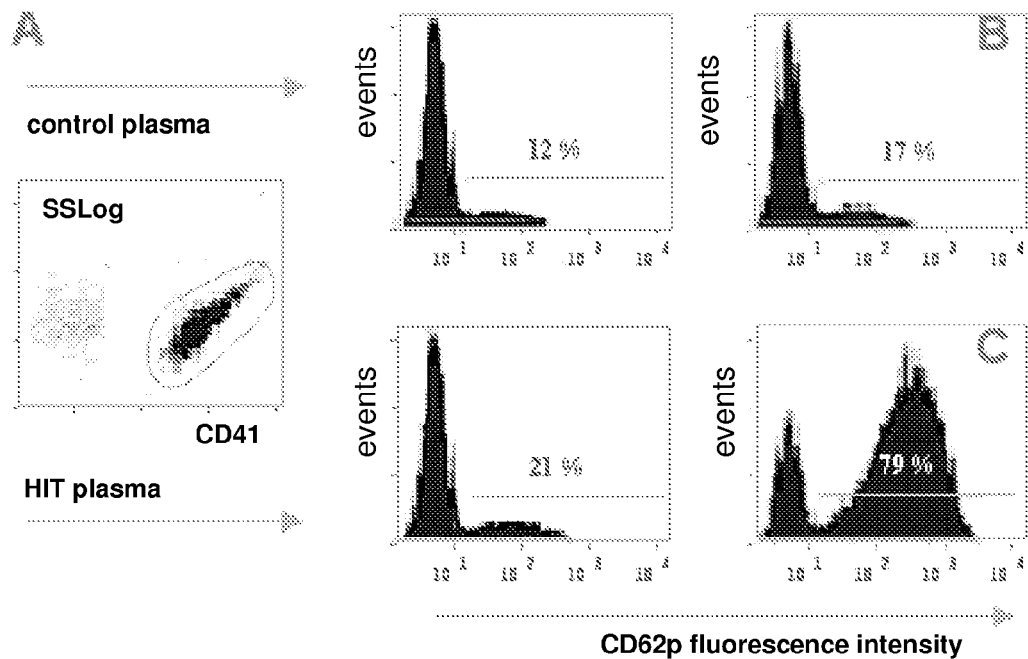
FIG. 3 shows in vitro activation of platelets by HIT ab positive plasma with heparin. A. Platelets gated on side scatter (SS log) and CD41 activity. Percentages of cells staining with CD62p after addition of heparin in the absence (B) or presence (C) of HIT ab positive plasma. The interface channel for positivity was set at the point where less than 2% of the control fluorescence was positive.
Figure 4:
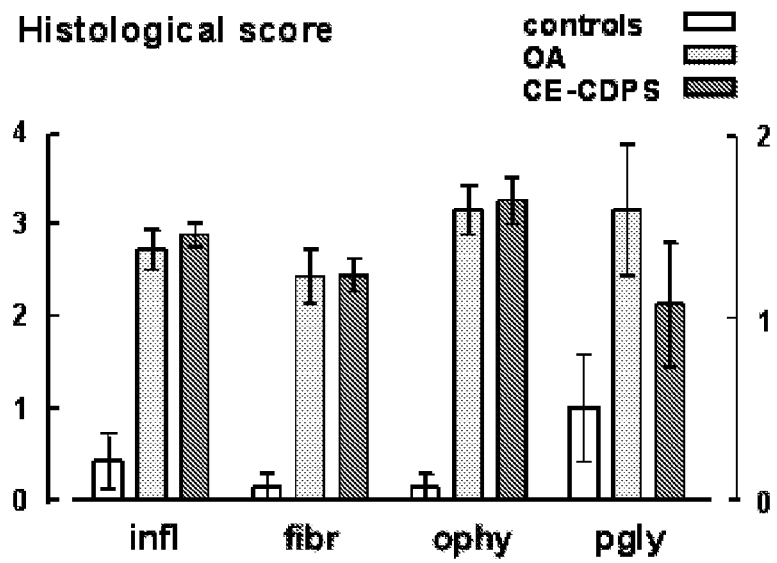
FIG. 4 shows the effect of CE-CDPS on the histology of an osteoarthritic joint. Inflammation (infl), fibrosis (fibr), osteophytes (ophy) and proteoglycan depletion (pgly) were scored on healthy control joints, saline-treated OA joints and CE-CDPS-treated OA joints. Left ordinate: histological score for infl, fibr and ophy. Right ordinate: score for pgly. Means (bars) ±1 SEM are presented.

The invention claimed is:

1. A β-cyclodextrin polysulfate compound represented by the structural formula

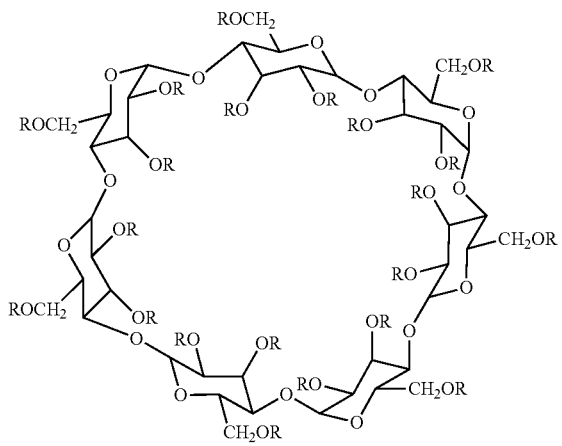

wherein each R group is independently chosen to be either —$CH_2$—$CH_2$—COOH, —$SO_3H$, or H, wherein from one to three R groups are —$CH_2$—$CH_2$—COOH, and wherein at least two R groups per glucopyranose unit are —$SO_3H$ and pharmaceutically acceptable salts thereof.

2. A β-cyclodextrin polysulfate compound according to claim 1, wherein the entire set of substituting groups R together comprise three —$CH_2$—$CH_2$—COOH groups, seventeen —$SO_3H$ groups, and one hydrogen.

3. A β-cyclodextrin polysulfate compound according to claim 1, wherein the entire set of substituting groups R together comprise three —$CH_2$—$CH_2$—COOH groups and eighteen —$SO_3H$ groups.

4. A β-cyclodextrin polysulfate compound according to claim 1 wherein an average from 2.00 to 2.57 R groups per glucopyranose unit comprise —$SO_3H$.

5. A β-cyclodextrin polysulfate compound according to claim 1 wherein an average from 2.2 to 3.0 R groups comprise —$CH_2$—$CH_2$—COOH.

6. A process for the preparation of a β-cyclodextrin polysulfate compound comprising:

providing a β-cyclodextrin compound represented by the structural formula

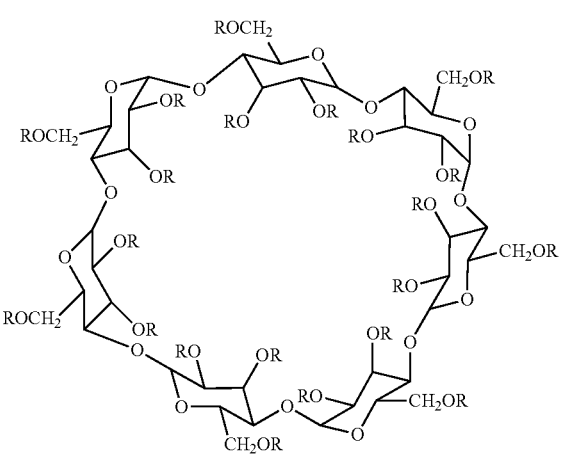

wherein each R group is independently chosen to be either —CH$_2$—CH$_2$—COOH or H, and wherein from one to three R groups are —CH$_2$—CH$_2$—COOH;

reacting said β-cyclodextrin compound with a sulfonating agent, wherein the amount of said sulfonating agent is such that said reaction converts at least two H per glucopyranose unit into —SO$_3$H groups.

7. A process according to claim 6, wherein said reaction is performed at a temperature within a range from 40° C. to 100° C.

8. A process according to claim 6 further comprising:
preparing said β-cyclodextrin compound by reacting β-cyclodextrin with acrylamide in an amount such that said reaction converts from one to three hydroxyl groups of said β-cyclodextrin into —CH$_2$—CH$_2$—COOH groups.

9. A process according to claim 8, wherein said reaction is performed at a temperature within a range from 40° C. to 95° C.

10. A process according to claim 8 wherein the molar ratio of acrylamide to β-cyclodextrin is within a range from 1 to 100.

11. A pharmaceutical composition comprising at least one β-cyclodextrin polysulfate compound according to claim 1 in combination with one or more non-toxic, pharmaceutically acceptable excipients.

12. A pharmaceutical composition according to claim 11, further comprising one or more additional active ingredients selected from the group consisting of anti-thrombotic agents, anti-coagulants, anti-inflammatory agents, cell products and anti-platelet-aggregating agents.

13. A pharmaceutical composition according to claim 12, wherein said additional active ingredient is selected from the group consisting of dipyridamole, aspirin, ticlopidine, clopidogrel and antagonists of the glycoprotein IIb/IIIa-complex.

14. A method of treating degenerative joint diseases, osteoarthritis, articularrheumatism, arthrosis or degenerative arthritis, or heparin-induced thrombocytopenia comprising:

administering a β-cyclodextrin polysulfate compound represented by the structural formula

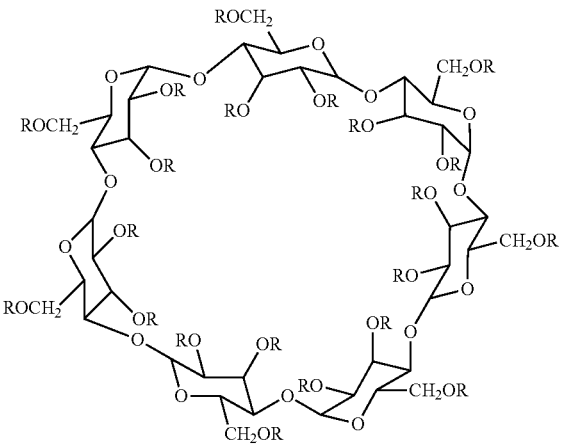

wherein each R group is independently chosen to be either —CH$_2$—CH$_2$—COOH, —SO$_3$H or H, wherein from one to three R groups are —CH$_2$—CH$_2$—COOH, and wherein at least two R groups per glucopyranose unit are —SO$_3$H and pharmaceutically acceptable salts thereof.

* * * * *